United States Patent [19]

D'Couto

[11] Patent Number: 5,194,814

[45] Date of Patent: Mar. 16, 1993

[54] ELECTROLYTIC CONDUCTIVITY DETECTOR

[75] Inventor: Silvester D'Couto, Austin, Tex.

[73] Assignee: Tremetrics, Inc., Austin, Tex.

[21] Appl. No.: 703,881

[22] Filed: May 22, 1991

[51] Int. Cl.$^5$ .......................................... G01N 27/02
[52] U.S. Cl. ............................... 324/446; 324/450; 204/277; 422/82.02; 436/150
[58] Field of Search ............ 324/439, 446, 449, 450; 204/277, 412; 422/82.02; 436/150

[56] References Cited

U.S. PATENT DOCUMENTS

| | | | |
|---|---|---|---|
| B1 4,032,296 | 1/1987 | Hall | 23/253 |
| 557,109 | 3/1896 | Cochrane | |
| 1,807,821 | 6/1931 | Behr | |
| 1,813,637 | 7/1931 | Powers | |
| 2,221,307 | 11/1940 | Christie | 175/182 |
| 2,258,045 | 10/1941 | Christie | 175/183 |
| 2,593,878 | 4/1952 | Haines | 23/232 |
| 2,768,135 | 10/1956 | Adelson | 422/82.02 X |
| 2,810,879 | 10/1957 | Cade | 324/30 |
| 2,813,833 | 11/1957 | Revallier | 352/321 |
| 2,863,736 | 12/1958 | Axt | 23/254 |
| 2,953,441 | 9/1960 | Clauss | 23/255 |
| 2,961,064 | 11/1960 | Fisher | 183/80 |
| 2,991,647 | 7/1961 | Harris | 73/23 |
| 3,001,917 | 9/1961 | Scheirer | 204/1 |
| 3,031,272 | 4/1962 | Agerbek-Poulsen | 23/254 |
| 3,080,746 | 3/1963 | Nerheim | 73/53 |
| 3,111,392 | 11/1963 | Stout | 23/255 |
| 3,158,446 | 11/1964 | Sternberg et al. | 23/254 |
| 3,271,111 | 9/1966 | Eoyd | 23/230 |
| 3,287,631 | 11/1966 | Stout | 324/30 |
| 3,308,648 | 3/1967 | Moulton | 73/23 |
| 3,309,845 | 3/1967 | Coulson | 55/228 |
| 3,322,500 | 5/1967 | Sternberg | 23/253 |
| 3,346,341 | 10/1967 | Sternberg | 23/230 |
| 3,506,824 | 4/1970 | Beroza | 250/43.5 |
| 3,527,571 | 9/1970 | Neuberger et al. | 204/277 X |
| 3,544,278 | 12/1970 | Bowman et al. | 23/254 |
| 3,594,294 | 7/1971 | Pretorius et al. | 204/180 |
| 3,640,822 | 2/1972 | Hrdina | 210/65 |
| 3,649,498 | 3/1972 | Pretorius et al. | 204/180 |
| 3,694,162 | 9/1972 | Kurz et al. | 23/253 |
| 3,759,816 | 9/1973 | Pretorius et al. | 204/299 |
| 3,838,971 | 10/1974 | Albertson | 23/232 |
| 3,854,881 | 12/1974 | Cohen | 23/253 |
| 3,924,180 | 12/1975 | Salzman et al. | 324/71 |
| 3,934,193 | 1/1976 | Hall | 324/30 |
| 3,936,729 | 2/1976 | Winslow, Jr. | 324/437 X |
| 3,953,790 | 4/1976 | Ebling et al. | 324/446 |
| 4,003,705 | 1/1977 | Buzza | 23/230 |
| 4,032,296 | 6/1977 | Hall | 23/253 |
| 4,183,791 | 1/1980 | Schick | 204/56 |
| 4,209,299 | 6/1980 | Carlson | 422/82.02 X |
| 4,295,856 | 10/1981 | Anderson | 23/232 |

(List continued on next page.)

FOREIGN PATENT DOCUMENTS 2536394 8/1975 Fed. Rep. of Germany .
537486 6/1941 United Kingdom .
1398947 6/1975 United Kingdom .

OTHER PUBLICATIONS

Gupta, S. R. and Hills, G. J. "A Precision Electrode-less Conductance Cell for Use at Audio-Frequencies" *Journal of Scientific Instruments*, vol. 33, Aug. 1956, pp. 313 and 314.

(List continued on next page.)

*Primary Examiner*—Jack B. Harvey
*Assistant Examiner*—Glenn W. Brown
*Attorney, Agent, or Firm*—Stroufe, Zamecki, Payne & Lundeen

[57] ABSTRACT

An electrolytic conductivity detector cell featuring a flow bore for communicating gaseous products of a gas chromatographic system designed to provide electrolytic conductivity supporting compounds, combined with a liquid solvent in which the compounds in question dissolve. Electrodes are provided, in general, in the form of conducting pins which are positioned in bores in the cell block, intersecting the flow bore to expose surfaces of the electrodes to the fluids in the bore.

12 Claims, 3 Drawing Sheets

U.S. PATENT DOCUMENTS

| | | | |
|---|---|---|---|
| 4,311,586 | 1/1982 | Baldwin | 210/101 |
| 4,358,423 | 11/1982 | Nedetzky | 422/68 |
| 4,362,994 | 12/1982 | Goldsmith | 324/449 |
| 4,414,091 | 11/1983 | Axenko et al. | 204/277 |
| 4,440,726 | 4/1984 | Coulson | 422/89 |
| 4,555,383 | 11/1985 | Hall | 422/89 |
| 4,649,124 | 3/1987 | Hall | 436/150 |
| 4,749,657 | 6/1988 | Takahashi et al. | 436/150 X |
| 4,804,846 | 2/1989 | Hall | 250/379 |
| 4,917,709 | 4/1990 | Hall | 55/18 |

OTHER PUBLICATIONS

Piringer, O. and Pascalau, M. "A New Detector for Gas Chromatography" *Journal of Chromatography*, vol. 8, 1962, pp. 410–412 (English translation included).

Sternberg, J. C. "Detection Devices for Gas Chromatography" Fourth International Gas Chromatography Symposium (Proceedings), Instrument Society of America, Jun. 17–21, 1963, Michigan State University, pp. 67–81.

Piringer, O., Tataru, E. and Pascalau, M. "Construction and Operation of the Electrolytic Conductivity Detector" *Journal of Gas Chromatography*, Mar., 1964, pp. 104–106.

Coulson, D. M. "Electrolytic Conductivity Detector for Gas Chromatography" *Journal of Gas Chromatography*, Apr., 1965, pp. 134–137.

Coulson, D. M. "Selective Detection of Nitrogen Compounds in Electrolytic Conductivity Gas Chromatography" *Journal of Gas Chromatography*, Aug., 1966, pp. 285–287.

Anderson, R. J. and Hall, R. C. "Hall Bipolar Pulse, Differential Electrolytic Conductivity Detector for GC: Design and Applications" *American Laboratory*, Feb. 1980, 9 pages.

Piringer, O. and Wolff, E. "New Electrolytic Conductivity Detector for Capillary Gas Chromatography" *Journal of Chromatography*, vol. 284, 1984, pp. 373–380.

"New Environmental Analyzer" one-page promotional literature from Hewlett-Packard, Winter, 1987.

Mohnke, M., Piringer, O. and Tataru, E. "Analysis of the Isotope Molecules of Hydrogen Using Capillary Columns and an Electrolytic Conductivity Detector" *Journal of Gas Chromatography*, vol. 6, Feb. 1968, pp. 117–119.

Jones, P. and Nickless, G. "Versatile Electrolytic Conductivity Detector for Gas Chromatography" *Journal of Chromatography*, vol. 73, 1972, pp. 19–28.

Hall, R. C. "A Highly Sensitive and Selective Microelectrolytic Conductivity Detector for Gas Chromatography" *Journal of Chromatographic Science*, vol. 12, Mar. 1974, pp. 152–160.

Lawrence, F. and Sen, N. P. "Simple Water Flow Control for the Coulson Electrolytic Conductivity Detector" *Analytical Chemistry*, vol. 47, No. 2, Feb. 1975, pp. 367 and 368.

"Tracor Hall ® Model 1000 Electrolytic Conductivity Detector" four-page promotional literature from Tracor instruments (now Tremetrics, Inc.).

"High Performance Detectors for Gas Chromatography" eight-page promotional literature from Tracor Instruments (now Tremetrics, Inc.).

MacDonald, J. and King, J. W. "Improved Hall Conductivity Detection System without Selvent Interference" *Journal of Chromatography*, vol. 124, 1976, pp. 364–368.

Coulson Electrolytic Conductivity Detector Operation and Service Manual, Mar., 1971, from Tracor Instruments Austin, Inc. (now Tremetrics, Inc.).

Model 700 Hall Electrolytic Conductivity Detector Operation and Service Manual, revised Nov. 1980, from Tracor Instruments Austin, Inc. (now, Tremetrics, Inc.).

700A Hall Electrolytic Conductivity Detector and 710 Total Halogen/Total Sulfur Systems Operation Manual, revised Dec. 1987, from Tracor Instruments Austin, Inc. (now Tremetrics, Inc.).

Tremetrics Model 1000 Hall ® Detector System Operation and Service Manual, revised Aug. 1991, from Tremetrics, Inc.

4420 Electrolytic Conductivity Detector, manual from O.I. Corporation, Jul., 1988.

*Chemical Engineers' Handbook* "Chromatographic Separations" pp. 16–39 to 16–42, McGraw-Hill (R. H. Perry, Consultant 5th ed. 1973).

"This is DELRIN ® AF Fiber Resin" 3-page informational literature from E. I. Du Pont de Nemours & Co. (Inc.).

"Kel-F ™ 81 PCTFE 3M Engineering Manual" 2-page introductory information from 3M publication.

"Properties of Vespel ® Parts" 4-page informational literature from E. I. Du Pont de Nemours & Co. (Inc.).

Coulson, D. M. and Cavanagh, L. A. "Automatic Chloride Analyzer" *Analytical Chemistry*, vol. 32, No. 10, Sep., 1960, pp. 1245–1247.

Coulson, D. M., Cavanagh, L. A., DeVries, J. E. and Walther, B. "Microcoulometric Gas Chromatography of Pesticides" *Journal of Agricultural and food Chemistry*, vol. 8, No. 5, Sep.–Oct. 1960, pp. 399–402.

OTHER PUBLICATIONS

Piringer, O. and Tataru, E. "Der Elektrolytleitfähig-keitsdetektor Konstraktion, Arbeitsweise und Anwendung" Gas-Chromatographic 1965, conference in Berlin, May 18-21, 1965, pp. F.329-F334. (no translation).

Coulson, D. M. "Electrochemical Detectors for Trace Determination of Nitrogen, Habide, Sulfur, and Carbon with GC" *American Laboratory*, May, 1969, pp. 22-32.

Patchett, G. G. "Evaluation of the Electrolytic Conductivity Detector for Residue Analyses of Nitrogen-Containing Pesticides" *Journal of Chromatographic Science*, vol. 8, Mar., 1970, pp. 155-158.

Rhoades, J. W. and Johnson, D. E. "Gas Chromatography and Selective Detection of N-Nitrosamines" *Journal of Chromatographic Science*, vol. 8, Oct., 1970, pp. 616 and 617.

Selucky, M. L. "Specific Gas Chromatography Detectors Part II: Electrolytic Conductivity Detector" *Chromatographia* 5, 1972, pp. 359-366.

Dolan, J. W., Hall, R. C. and Todd, T. M. "Selective Detection of Chlorinated Insecticides in the Presence of Polychlorinated Biphenyls" *Journal of the Association of Official Analytical Chemists*, vol. 55, No. 3, May, 1972, pp. 537 and 538.

Dolan, J. W. and Hall, R. C. "Enhancement of the Sensitivity and Selectivity of the Coulson Electrolytic Conductivity Detector to Chlorinated Hydrocarbon Pesticides" *Analytical Chemistry*, vol. 45, No. 13, Nov. 1973, pp. 2198-2204.

Hall, R. C. and Risk, C. A. "Rapid and Selective Determination of Free Barbituates by Gas Chromatography Using the Electrolytic Conductivity Detector" *Journal of Chromatographic Science*, vol. 13, Nov., 1975, pp. 519-524.

Garwin, E. L. and Roder, A. "Electrolytic Conductivity Detector for Trace Analysis of $H_2$, HD, $D_2$ and Neon in Hydrogen and Deuterium" *Journal of Chromatographics Science*, vol. 14, Nov., 1976, pp. 541-545.

Risk, C. A. and Hall, R. C. "Evaluation of the Hall Electrolytic Conductivity Detector for the Analysis of Narcotic Alkaloid and Phenothiazine Drugs Extracted from Urine" *Journal of Chromatographic Science*, vol. 15, May, 1977, pp. 156-159.

Hall, R. C. "The Nitrogen Detector in Gas Chromatography" *Critical Reviews TM* in Analytical Chemistry, vol. 7, Issue 4, Dec., 1978 pp. 323-380.

Hall, R. C. and Harris, D. E. "Direct Gas Chromatographic Determination of Carbamate Pesticides Using Carbowax 20M-Modified Supports and the Electrolytic Conductivity Detector" *Journal of Chromatography* vol. 169, pp. 245-259.

Ottmers, D. M., Jr., Jones, D. C., Keith, L. H. and Hall, R. C. "Instruments for Environmental Monitoring" *Chemical Engineering*, Deskbook Issue, Oct. 15, 1979, pp. 85-96.

Ehrlich, B. J., Hall, R. C., Anderson, R. J. and Cox, H. G. "Sulfur Detection in Hydrocarbon Matrices. A comparison of the Flame Photometric Detector and the 700A Hall TM Electrolytic Conductivity Detector" *Journal of Chromatographic Science*, vol. 19, May, 1981, pp. 245-249.

Lopez-Avil, V. and Northcutt, R. "Application of the Hall TM Electrolytic Conductivity Detector for the Analysis of Chloroanilines and Chloronitroanilines in POTW Sludges" *Journal of High Resolution Chromatography and Chromatography Communications*, vol. 5, Feb. 1982, pp. 67-74.

Gluck, S. "Performance of the Model 700A Hall TM Electrolytic Conductivity Detector as a Sulfur-Selective Detector" *Journal of Chromatographic Science*, vol. 20, Mar., 1982, pp. 103-108.

Gibb, T. B., and Wolfe, P. H. "Determination of Parts-per-Billion Vinyl Chloride Monomer in Vinyl Chloride Copolymers by Use of an Automated Headspace Analyzer with an Electrolytic Conductivity Detector" *Journal of Chromatographic Science*, vol. 20, Oct., 1982, pp. 471-474.

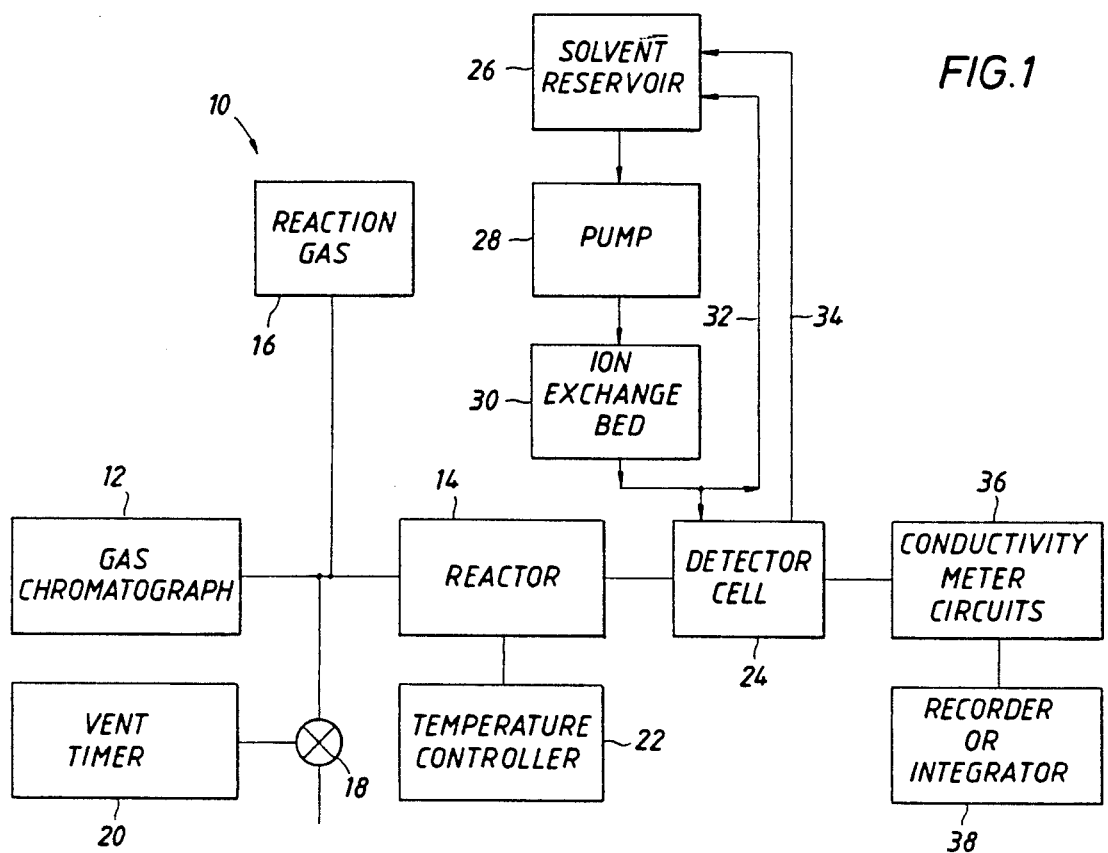
FIG.1
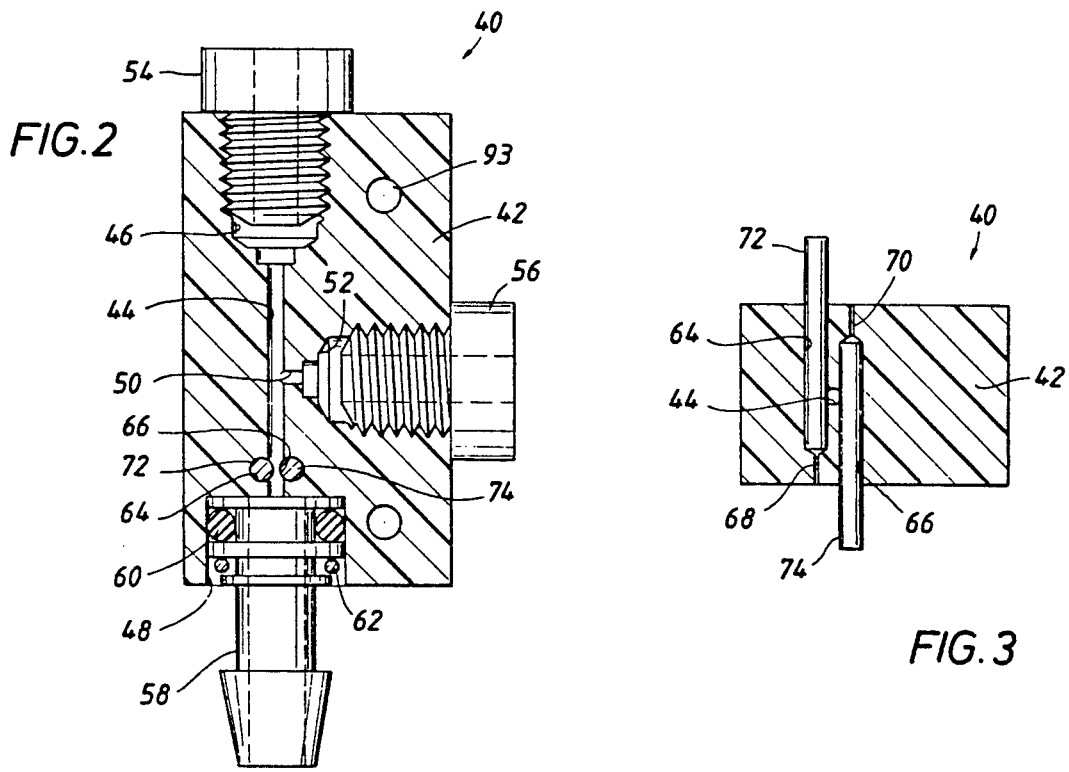
FIG.2
FIG.3

5,194,814

ELECTROLYTIC CONDUCTIVITY DETECTOR

BACKGROUND OF THE INVENTION

1. Field of the Invention

The present invention pertains to methods and apparatus for obtaining conductivity information for fluids. More particularly, the present invention relates to techniques for measuring electric current through fluid containing electrolytes. As disclosed, the present invention is embodied in an electrolytic conductivity detector (ELCD), and particularly in an ELCD cell in which current is passed through the fluid whose conductivity is to be determined, and finds particular application in a detector system for gas chromatography.

2. Description of Prior Art

The application of electrolytic conductivity for the determination of gas chromatographic eluates is generally known. For example, U.S. Pat. Nos. 3,309,845, 3,934,193 and 4,555,383 disclose ELCD cells for use in gas chromatography.

It is advantageous and desirable to provide an ELCD system, particularly for use in a gas chromatographic system, which is reliable and sensitive, and which provides high resolution and repeatability. It is thus an object of the present invention to provide an ELCD cell for use in a detection system, and particularly as part of a gas chromatographic system, which is also readily maintained and provides sufficient signal-to-noise ratio for chromatography.

SUMMARY OF THE INVENTION

The present invention provides an electrolytic conductivity detector cell including a cell block generally of insulating material, and having a flow bore extending through the block and ending in an outlet. A first inlet communicates with the flow bore whereby liquid may enter the flow bore and move along the bore to the outlet. A second inlet communicates with the flow bore whereby gas may enter the flow bore and intersect liquid therein at an intersection location, and move along the flow bore to the outlet. A first electrode intersects the flow bore and extends partially into the flow bore to provide a first surface of intersection with the interior of the flow bore at a first axial location along the flow bore. A second electrode intersects the flow bore and extends partially into the flow bore to provide a second surface of intersection eith the interior of the flow bore at a second axial location along the flow bore. The first and second axial locations of intersection of the electrodes with the flow bore interior are between the outlet and the location of intersection for gas and liquid in the flow bore. The axial locations of the two electrodes along the flow bore may be the same or the electrodes may intersect the flow bore at different axial locations.

The eletrodes may be in the form of pins, or rods of any shape cross section, although round, or circular, cross sections provide pins which are relatively easy to manipulate and require no special angular orientation about their longitudinal axes. The pin eletrodes may be oriented transverse to the longitudinal axis of the flow bore, or at some acute angle relative to the axis of the flow bore. The pin electrodes may be oriented generally mutually parallel or at some non-zero acute angle relative to each other. The flow bore may be vertical, or at an acute angle relative to the horizontal. Variations in the shape of the pins, their orientations relative to the flow bore and to each other, and the orientation of the flow bore relative to the horizontal, for example, may be selected according to the desired interaction and contact of liquid in the flow bore with the electrodes. Additionally, the transverse dimension of the flow bore, the transverse dimensions of the electrodes and the extent to which the electrodes extend within the interior of the flow bore may likewise be selected to affect the interaction of the liquid with the electrodes, to enhance the determination of conductivity of the liquid accordingly.

A detector cell according to the present invention may also include two reference electrodes intersecting the flow bore and being exposed to the interior thereof between the inlet for liquid and the location for intersection of gas and liquid in the flow bore. The reference electrodes may be used for obtaining reference conductivity levels for liquid prior to exposure to the gas input to the flow bore. A constriction in the flow bore operates to prevent gas from moving against the liquid flow to reach the liquid inlet or reference electrodes.

BRIEF DESCRIPTION OF THE DRAWINGS

FIG. 1 is a block diagram of a gas chromatographic system with an electrolytic conductivity detector system;

FIG. 2 is a side elevation, in partial section, of a detector cell according to the present invention, with pin electrodes transverse to the flow bore;

FIG. 3 is a top plan view, in partial section, of the detector cell of FIG. 2;

DESCRIPTION OF PREFERRED EMBODIMENTS

Figure 4:
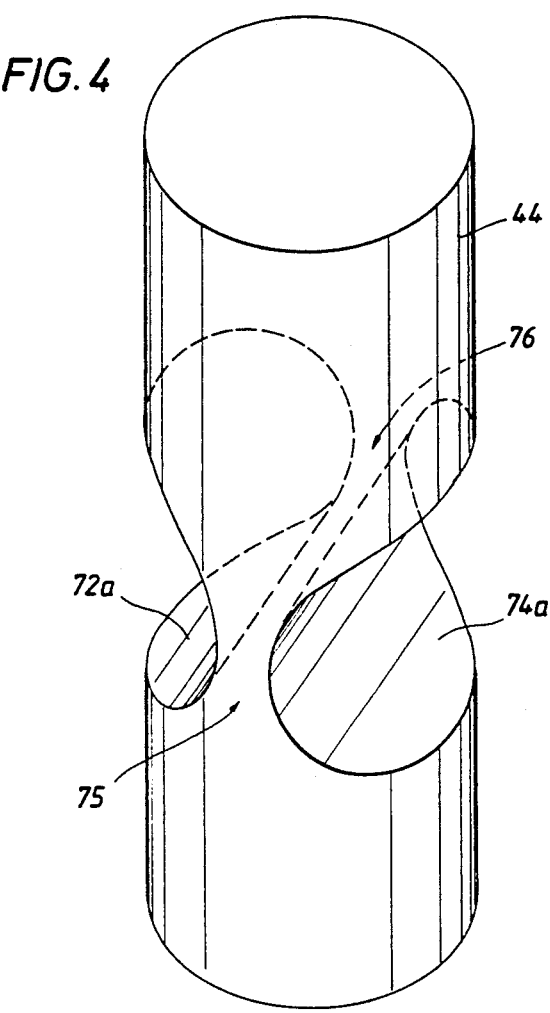
FIG. 4 is a fragmentary perspective view of the flow bore of the detector cell of FIGS. 2 and 3, showing the surfaces of intersection of the bore with the electrodes.

A gas chromatography system with an ELCD system is show in block diagram form generally at 10 in FIG. 1. Output gases from a gas chromatograph 12 are conveyed to a reactor furnace 14, or other device for the formation of inorganic compounds that will support electrolytic conductivity. Gas from an appropriate reaction gas source 16 is utilized in processing the gaseous compounds in the reactor 14. The reaction gas source 16 is preferably connected to the reactor 14 through a conventional valve (not shown). The type of reaction gas utilized depends on the mode in which the system is operated, or, in other words, the compounds of interest. Hydrogen and air, for example, are reaction gases used for different modes of operation while helium is a typical carrier gas used.

Normally, a sample to be tested is injected into the gas chromatograph 12 dissolved in a volatile solvent which usually exits the gas chromatograph column before any of the compounds of interest. The relatively large amount of solvent might, after repeated injections, tend to coat the surface of the reaction tube 14 and so preclude the desired catalytic action. For this reason, a solenoid vent valve 18 is provided to open at the time of injection of the sample into the gas chromatograph 12, and the valve remains open until virtually all the solvent has been ejected. The valve 18 is then closed, and compounds of interest are driven into the reactor 14 by the carrier gas. An electrical vent timer circuit 20 controls the opening and closing of the valve 18.

Operation of the reactor furnace 14 is controlled by a temperature controller electrical circuit 22. The gaseous reaction products formed in the reactor 14 are directed to the ELCD assembly, and especially to an ELCD cell 24. A scrubber (not shown) can be interfaced to the reaction tube 14 for removing unwanted reaction products.

A liquid solvent is also input to the detector cell 24, with the identity of the solvent depending on the mode of operation of the system. Typically, propanol, water or methanol are utilized as solvents. A solvent reservoir 26 is provided as a source of the solvent, and a pump 28 circulates the solvent from the reservoir and ultimately to the detector cell 24. Before entering the detector cell 24 the solvent passes through an ion exchange bed 30, typically containing one or more resins, for the purpose of cleaning the solvent and removing any electrically conducting materials. A return line 32 from the output of the ion exchange bed 30 is provided to the solvent reservoir 25. The return line 32 may be utilized if the solvent input capacity of the detector cell 24 is exceeded by the volumetric flow rate of solvent provided by the pump 28. A second return line 34 conveys liquid output from the detector cell 24 to the solvent reservoir 26 for reuse of the solvent. Conditioning of the reused solvent is assured by the ion exchange bed 30 before the solvent again enters the dectector cell 24.

Further details of the operation of a gas chromatograph system in general may be provided by reference to the aforementioned U.S. patents.

In the detector cell 24, gaseous output from the reactor 14, having possibly passed through a scrubber (not shown), contacts the solvent with the result that gaseous compounds able to support electrolytic conductivity are dissolved in the liquid. Undissolved gas and the solvent pass through a flow bore in the detector cell 24 past electrodes, whose construction is described in detail below. A conductivity meter circuit 36 is connected to the electrodes, and applies an appropriate drive signal to the electrodes. The generation of current through the flow bore between the electrodes is dependent on the conductivity of the material at the location of the electrodes, and the determination of the current flow is utilized with the meter circuits 36 to obtain a measure of the conductivity of the fluid at the detectors. Output information signals from the meter circuits 36 may be recorded or processed, for example, by a recorder or an integrator 38. Chromatograms can be obtained by the output device 38 in the usual fashion as is known in the field of gas chromatography.

An electrolytic conductivity detector cell according to the present invention is shown generally at 40 in FIG. 2. The cell 40 includes a cell block, or body, 42. The cell block 42 may be constructed of any appropriate material sufficiently inert to the solvent and gaseous materials to be introduced into the cell block, sufficiently wettable by the solvent used, and electrically non-conducting. Various polymers may be utilized to construct the cell block 42. Such materials for construction of the cell block 42 include the thermoplastic sold under the trade designation DELRIN® AF, the thermoplastic sold under the trade designation Kel-F ™ 81, which is a homopolymer of chlorotrifluoroethylene, and one or another of the SP polyimide or KS arimid resins sold under the trade designation Vespel® Parts.

The cell block 42 may be provided in the form of a rectangular parallelepiped, although the actual shape of the block is not critical for its operation. A cylindrical flow bore 44 passes through the block 42, extending from a liquid inlet 46 at one of the block, to an outlet 48 at the opposite end of the block. The flow bore 44 is intersected by a gas flow line 50 which extends from a gas inlet 52. The liquid inlet 46 is threaded as illustrated to receive a fitting 54 for attaching a liquid communication line (not shown) to the body 42 whereby liquid may be introduced into the flow bore 44 at the liquid inlet. Similarly, the gas inlet is threaded as illustrated for receiving a fitting 56 by which a gas line (not shown) may be connected to the block 42 whereby gas may be introduced into the flow bore 44. Threaded connection of each of the fittings 54 and 56 with the block 42 fluid-seals the fitting to the block. Such sealing between the fittings 54 and 56 and the block 42 is sufficient to prevent leakage of any fluid out of the block at the inlets 46 and 52, respectively, under any fluid pressure conditions under which the cell 40 is utilized.

An outlet fitting 58 is received in the outlet 48, and an appropriate tubing (not shown), for example, may be engaged over the open end of the outlet fitting for conveying away from the detector the liquid and gas flowing through the flow bore 44 and exiting the block 42. Liquid solvent may be tapped off of the output passing through the fitting 58 for return to the solvent reservoir 26 as indicated in FIG. 1, for example. The fitting 58 features a flow passage significantly wider than the flow bore 44, and therefore is not subject to any significant fluid pressure tending to dislodge the fitting from the cell block 42. Nevertheless, a fluid-tight seal between the fitting 58 and the cell block 42 is provided by an elastomeric seal, such as an O-ring seal, 60 carried in an appropriate groove in the fitting and engaging the interior wall of the outlet 48. The fitting 58 may be maintained in place within the outlet 48 merely by friction. However, further securing of the fitting 58 within the outlet 48 may be provided by one or more pins 62 inserted in appropriate bores through the body 42 after the fitting is in place within the outlet. A pin 62 may be in the form of a U-shaped retainer pin which passes through two such bores through the cell block 42. As shown, the pin or pins 62 block withdrawal of the fitting 58 from the outlet 48.

The cell block 42 further features two electrode bores 64 and 66, which pass partly through the extent of the body 42. Further appreciation of the extent and orientation of the electrode bores 64 and 66 may be had by reference to FIG. 3 wherein it may be seen that the electrode bores are formed with the assistance of pilot holes 68 and 70, respectively. The pilot holes 68 and 70 are significantly smaller diameter than the electrode bores 64 and 66, and may be prepared more accurately and with greater ease than the larger diameter bores without the aid of pilot holes. Thereafter, the larger diameter bores 64 and 66 may be more readily formed by use of a drill bit or other such device following the respective pilot holes.

The electrode bores 64 and 66 are formed to intersect the flow bore 44, and to receive pin electrodes 72 and 74, respectively. The pin electrodes 72 and 74 are generally in the form of cylindrical rods made of electrically conducting material, such as metal or an appropriate alloy, for example. The electrodes 72 and 74 are exposed to the gas and liquid in the flow bore 44, and, therefore, should be resistant to interaction with those fluids. Gold plated pins, for example, are preferred as the electrodes 72 and 74. The electrode bores 64 and 66 are shown as drilled or otherwise formed from opposite sides of the cell block 42, so that the corresponding electrodes 72 and 74 extend outwardly on opposite sides of the cell block. If desired, the electrode bores 64 and 66 may be formed from the same side of the cell block 42 so that the electrodes 72 and 74 protrude from the cell block on the same side. The extensions of the electrodes 72 and 74 beyond the surfaces of the cell block 42 are provided so that electrical connections can be made to the electrodes for communication with the conductivity meter circuits 36 indicated in FIG. 1, for example.

FIG. 4 is a representation of the interior surface of the flow bore 44 at the intersection of that surface with the electrode bores 64 and 66 and, therefore, with those portions of the electrodes 72 and 74 which extend into the flow bore. In particular, the surfaces of intersection of the flow bore 44 with the electrodes 72 and 74 are indicated in FIG. 4 at 72a and 74a, respectively. It will be appreciated that the extent of these surfaces of intersection 72a and 74a may be selectively varied by varying the diameter of the flow bore 44, by varying the diameter of one or both of the electrodes 72 and 74, by varying the position of one or both of the electrode bores 64 and 66 relative to the flow bore 44, or by varying the orientation of one of both of the electrode bores relative to the flow bore, for example. Although the electrodes illustrated herein are generally shown in cross section to be circular, electrodes of different cross sections may be utilized, such as squares, ellipses, triangles and rectangles, for example, thus varying the shape of the surfaces of intersection of the electrodes with the flow bore also.

It is believed that the conductivity measurement in an ELCD is effected through solvent, including electrolytic material, coming in contact with the electrodes and forming a bridge between them. It is further believed that, since the material of the cell block 42 is wettable by the solvents utilized, movement of a solvent including electrolytes along the flow bore 44 is at least accompanied by solvent in the form of a liquid film on the interior surface of the flow bore 44. If such a liquid film is the primary mechanism by which the liquid negotiates the flow bore 44 at the electrodes, and particularly if it is the only mechanism in a given case, then the measurement area, or region between the electrodes, wherein an electric current is established for the purpose of obtaining the conductivity of the liquid with electrolytes lies along the flow bore interior wall at the region where the electrodes are mutually closest, such as the area indicated in FIG. 4 at 75. With the surfaces of intersection 72a and 74a arranged generally symmetrically relative to the flow bore 44 as illustrated in FIG. 4, a like area of measurement between the electrodes at the surface of the flow bore 44 appears opposite the region 75, at the location indicated at 76.

Figure 5:
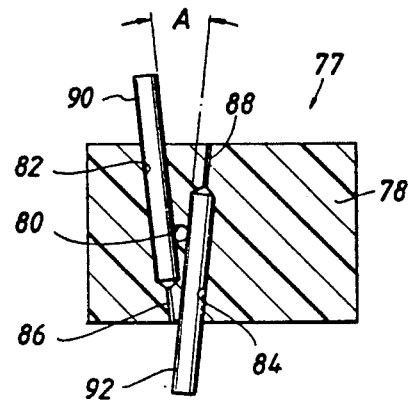
FIG. 5 is a top plan view, in partial section, of a detector cell, similar to FIG. 3, illustrating pin eletrodes transverse to the flow bore but oriented at a non-zero acute angle relative to each other.

Variation of any of the parameters indicated above to change the intersection surfaces 72a and 74a generally will alter the size and/or shape of the measurement areas 75 and/or 76. For example, FIG. 5 illustrates a detector cell 77 having a cell block 78 with an elongate flow bore 80 intersected by electrode bores 82 and 84. Pilot holes 86 and 88 are provided for the formation of the electrode bores 82 and 84, respectively, transverse to the flow bore 80, but intersecting the flow bore at different angles so that, in general, an acute angle A, greater than zero degrees, is formed between electrodes 90 and 92 positioned within the electrode bores. The corresponding measuring surfaces along the flow bore 80 and between the surfaces of intersection of that bore with the electrodes 90 and 92 are not equal in size. It is believed that, due to the relative closeness of the electrodes 90 and 92 toward the bottom of the flow bore 80 as viewed in FIG. 5, greater electric current will flow between the electrodes at the corresponding measuring surface than will flow between the electrodes on the opposite side of the flow bore 80.

Figure 6:
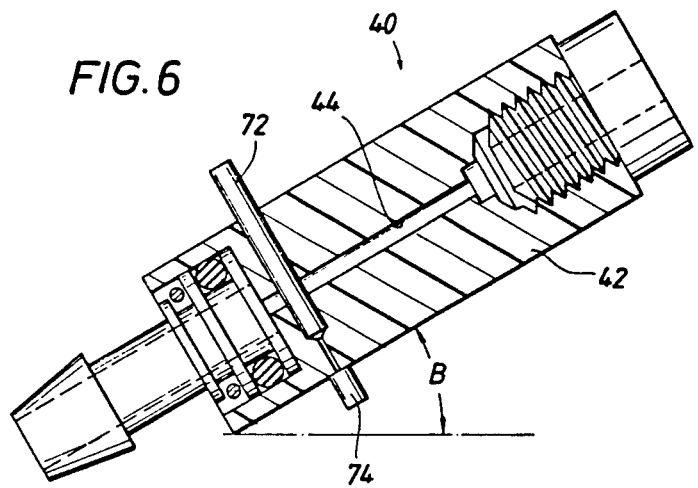
FIG. 6 is a front elevation, in partial section, of the detector cell as shown in FIGS. 2–4, but positioned so that the flow bore is tilted at an acute angle relative to the horizontal.

Yet another way of altering the effective measuring area between the electrodes is to tilt the cell block. Reference to FIG. 2 discloses that the cell block 42 is equipped with two additional bores, of holes, 93 which may receive implements for mounting the cell block, such as pins or screws, preferably of the self retained type. By means of the holes 93 the cell 40 may be suspended, or secured, in any desired orientation. In FIG. 6 the cell block 42 and, therefore, the flow bore 44, are oriented at an acute angle B relative to the horizontal. Then, the pin electrodes 72 and 74 transverse to the flow bore 44 are oriented at the acute angle of ninety degrees minus B relative to the horizontal. It will be appreciated, by reference to FIGS. 4 and 6, that the configuration of the flow bore 44 and the electrodes 72 and 74 illustrated in FIG. 6 tends to cooperate with the gravitational force on the liquid in the flow bore to cause more liquid to pass between the electrodes at the lower measuring surface along the flow bore than the opposite, higher measuring surface.

Figure 7:
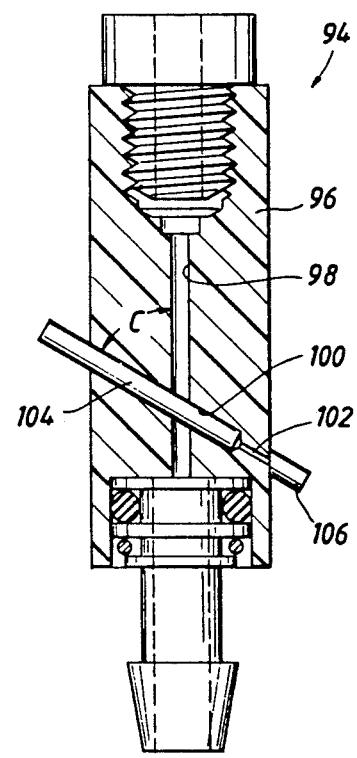
FIG. 7 is a front elevation, in partial section, of a detector cell with pin electrodes set at an acute angle relative to the flow bore.

FIG. 7 illustrates another variation of the manner of orienting the electrodes relative to the flow bore in a detector cell according to the present invention. A detector cell 94 is indicated in FIG. 7 having a cell block 96 and an elongate flow bore 98 therethrough. An electrode bore 100, formed with a pilot hole 102, intersects the flow bore 98 at an acute angle C. A pin electrode 104 resides in the electrode bore 100. A second pin electrode 106 is positioned within an electrode bore (not visible), and intersects the flow bore 98 on the opposite side thereof relative to the intersection of the bore with the electrode 104, again at the acute angle C. It will be appreciated that the two measuring areas between the electrodes 104 and 106 along the interior wall of the flow bore 98 occur at different axial positions along the flow bore, so that the measuring area to the left as viewed in FIG. 7 is upstream relative to the measuring area to the right as view in FIG. 7. Consequently, liquid film moving along the interior wall of the flow bore 98 reaches the upstream measuring area between the electrodes 104 and 106 before liquid film moving along the flow bore surface reaches the downstream measuring area between the same two electrodes. Some liquid may be deflected by the slant of the electrodes 104 and 106 generally along the electrodes and to the right as viewed in FIG. 7 with the result that liquid film at the downstream measuring area may be thicker than that at the upstream measuring area.

Figure 8:
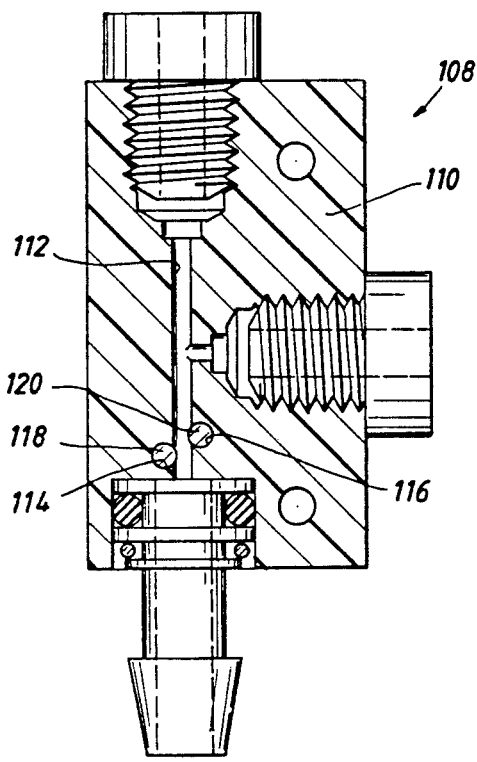
FIG. 8 is a side elevation, in partial section, of a dectector cell having electrodes staggered along the flow bore.

FIG. 8 illustrates yet another variation in the configuration of pin electrodes relative to a flow bore. A detector cell 108 in FIG. 8 has a cell block 110 and a flow bore 112 therethrough, intersected by two electrode bores 114 and 116, housing pin electrodes 118 and 120, respectively. The electrode bores 114 and 116 and, therefore, the electrodes 118 and 120, are staggered relative to the flow bore 112, that is, one electrode is positioned generally upstream along the flow bore relative to the other electrode. The two measuring surfaces along the wall of the flow bore 112 and between the electrodes 118 and 120 are then skewed relative to the longitudinal axis of the flow bore, but may otherwise be symmetrical relative to each other, or mirror images of each other. A liquid film moving along the interior wall of the flow bore 112 may contact the upstream electrode 120 before the film reaches the downstream electrode 118. By staggering the electrodes 118 and 120 relative to the flow bore 112 as illustrated in FIG. 8, the measuring areas may be increased in size, and in particular in the distance across between the electrodes, while the actual surface area of the electrodes intersecting the flow bore 112 remains the same as it would be if the electrodes were at the same axial location relative to the flow bore, as in the case of the detector cell illustrated in FIGS. 2-4, for example.

It will be appreciated that any combination of two or more techniques for affecting the measurement of conductivity in the fluid in the borehole of a detector cell according to the present invention, by varying the flow bore and/or one or both electrodes, may be utilized. For example, the electrodes may be oriented with respect to each other at an acute angle greater than zero degrees as illustrated in FIG. 5, in a staggered alignment as shown in FIG. 8, and/or with the cell block tilted as indicated in FIG. 6. The particular configurations, shapes, and sizes of the flow bore and electrodes may be chosen to enhance the reliability, repeatability, sensitivity and resolution, for example, of the electric current and conductivity measurements made utilizing a detector cell according to the present invention.

Figure 9:
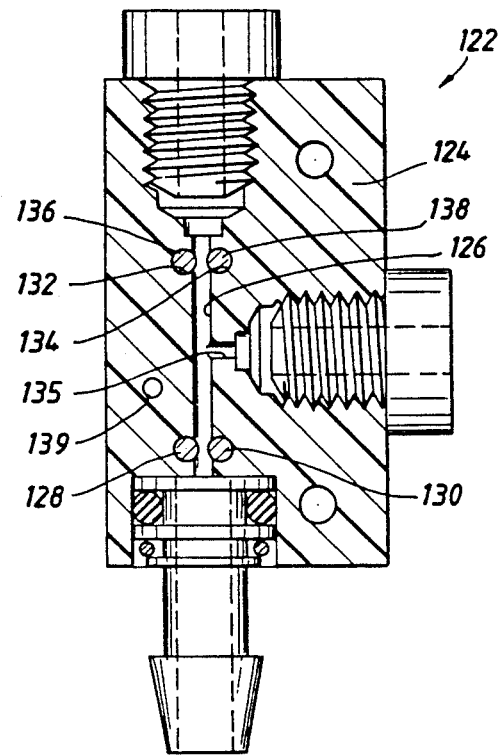
FIG. 9 is a side elevation, in partial section, of a detector cell similar to the detector cell of FIGS. 2–4, but having a pair of reference electrodes transverse to the flow bore toward the solvent inlet.

FIG. 9 shows a detector cell at 122, according to the present invention, including reference electrodes. The cell 122 has a cell block 124, similar to that of the detector cell 40 of FIGS. 2-4, including a flow bore 126 and two pin electrodes 128 and 130 transverse to the flow bore axis, again as shown in FIGS. 2-4. Additional electrode bores 132 and 134 are positioned in the cell block 124, transverse to and intersecting the flow bore 126 at a position upstream from the intersection of the flow bore with the gas flow line 135. The bores 132 and 134 are shown located at the same axial position along the flow bore 126. Pin electrodes 136 and 138 reside in the electrode bores 132 and 134, respectively. It will be appreciated that the pin electrodes 136 and 138, being exposed to the interior of the flow bore 126, may be contacted by fluid input to the cell block prior to contact of that fluid with gas input through the flow line 135. Consequently, a conductivity measurement made on the liquid solvent utilizing the upper electrodes 136 and 138 would be made free of any electrolytic material added by the gaseous input to the cell block 124 from the reactor 14 as indicated in FIG. 1. The upper electrodes 136 and 138 thus serve as reference electrodes, whereby a reference measurement can be made of the conductivity of the solvent free of the electrolytes provided by gas dissolved in the solvent within the flow bore 126. To constrast the electrodes, the lower electrodes 128 and 130 may be referred to as the analytical electrodes, for example, used to measure the conductivity of the solvent containing the electrolytes of interest.

In practice, a drive signal is impressed on the reference electrodes 136 and 138 as well as the analytical electrodes 128 and 130, and the difference in the conductivity between the analytical and reference electrode measurements is taken in determining the conductivity of the solvent as affected by the presence of electrolytes added due to the gas input through the flow line 135. For convenience, a common, or ground electrode 139 is provided in an appropriate bore in the cell block 124 to which, for example, analytical electrode 128 and reference electrode 136 are electrically connected.

Figure 10:
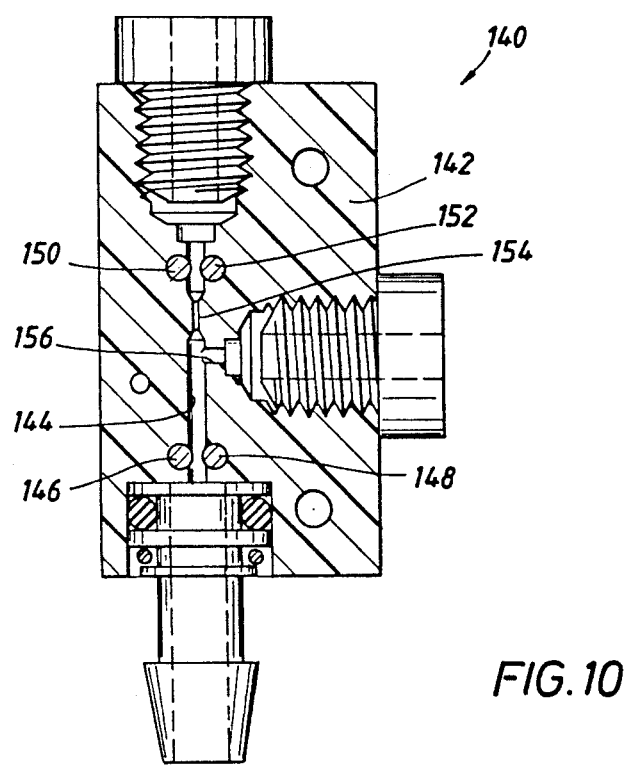
FIG. 10 is a side elevation, in partial section, of a detector cell with reference electrodes as shown in FIG. 9, but featuring a constriction in the flow bore.

FIG. 10 shows a detector cell 140 according to the present invention, having a cell block 142 with a flow bore 144 and analytical electrodes 146 and 148 along with reference electrodes 150 and 152, generally positioned as in the case of the cell 122 in FIG. 9. However, the flow bore 144 features a constriction 154 between the reference electrodes 150, 152 and the intersection of the flow bore with the gas line 156. The purpose of the constriction 154 is to prevent any gas entering the flow bore 144 from the gas line 156 from reaching the reference electrodes 150 and 152 in the event that input gas pressure and volumetric flow rate are sufficiently large to permit the gas to move upstream against the flow of the input liquid solvent.

The present invention thus provides a detector cell, for use in an electrolytic conductivity detector system, particularly applicable to a gas chromatographic system, wherein the electrodes are provided in the form of pins, or rods, that intersect the flow bore through the detector cell and are exposed to the fluid moving along the flow bore for the purpose of establishing an electric current through the fluid whereby the conductivity of the fluid may be determined. The flow bore and the electrodes may be selected to facilitate this measurement.

The foregoing disclosure and description of the invention is illustrative and explanatory thereof, and various changes in the size, shape and materials as well as in the details of the illustrated construction may be made within the scope of the appended claims without departing from the sprit of the invention.

What is claimed is:

1. An electrolytic conductivity detector cell comprising:
   a. a cell block, at least in part of electrically insulating material;
   b. a flow bore extending through the block and ending in an outlet;
   c. a first inlet whereby liquid may enter the flow bore and move therealong to the outlet;
   d. a second inlet whereby gas may enter the flow bore and intersect the liquid therein at an intersection location, and move along the flow bore to the outlet;
   e. a first elongate electrode intersecting the flow bore and extending sideways partially therein to provide with a portion of the side surface of the first electrode, a first surface of intersection with the interior of the flow bore at a first axial location along the flow bore;

f. a second elongate electrode intersecting the flow bore and extending sideways partically therein to provide with a portion of the side surface of the second electrode, a second surface of intersection with the interior of the flow bore at a second axial location along the flow bore; and g. the first and second axial locations are between the outlet and the location of intersection for gas and liquid in the flow bore.

2. A detector cell as defined in claim 1 wherein the first and second electrodes are provided in the form of elongate pins.

3. A detector cell as defined in claim 2 wherein the pins are oriented to define an acute angle therebetween greater than zero degrees.

4. A detector cell as defined in claim 2 wherein at least one pin is oriented transverse to the longitudinal axis of the flow bore.

5. A detector cell as defined in claim 2 wherein at least one pin is oriented relative to the longitudinal axis of the flow bore at an acute angle greater than zero degrees.

6. A detector cell as defined in claim 2 wherein at least one pin is circular in cross section.

7. A detector cell as defined in claim 1 wherein the flow bore is oriented at an acute angle relative to the horizontal.

8. A detector cell as defined in claim 1 further comprising a pair of reference electrodes, intersecting the flow bore at locations between the first inlet for liquid and the location of intersection for gas and liquid in the flow bore.

9. A detector cell as defined in claim 8 further comprising a constriction in the flow bore between the locations of the intersection of the reference electrodes with the flow bore and the location of intersection for gas and liquid in the flow bore.

10. A detector cell as defined in claim 1 further comprising a constriction in the flow bore between the location of intersection for gas and liquid in the flow bore and the first inlet for liquid.

11. A detector cell as defined in claim 1 wherein the first and second axial locations are at the same location along the flow bore.

12. A detector cell as defined in claim 1 wherein the first and second axial loacations are at different locations along the flow bore.

* * * * *

UNITED STATES PATENT AND TRADEMARK OFFICE
CERTIFICATE OF CORRECTION

PATENT NO. : 5,194,814
DATED : March 16, 1993
INVENTOR(S) : Silvester D'Couto

It is certified that error appears in the above-identified patent and that said Letters Patent is hereby corrected as shown below: On the title page: Item [56] Other Publications column 2, after the listing beginning with "Tremetrics Model 1000 Hall® Detector System Operation and Service Manual, Revised Aug. 1991, from Tremetrics, Inc." and before the listing "4420 Electrolytic Conductivity Detector, Manual from O.I. Corporation, Jul. 1988." the following reference should be inserted:

-- 9000 Gas Chromatograph Manual, Revision A, Sept. 1990, Section VI e, Hall® Electrolytic Conductivity Detector, cover sheet and pages 6E-1 to 6E-32. --.

column 2, reference 3, beginning with "Tracor Hall® Model 1000" and ending with "[Tremetrics, Inc.]" the word "instruments" should be capitalized and read -- Instruments --.

UNITED STATES PATENT AND TRADEMARK OFFICE
CERTIFICATE OF CORRECTION

PATENT NO. : 5,194,814

DATED : March 16, 1993

INVENTOR(S) : Silvester D'Couto

It is certified that error appears in the above-identified patent and that said Letters Patent is hereby corrected as shown below:

column 2, reference 5, beginning "MacDonald" and ending with "364-368." the word "selvent" should be changed to read -- solvent --.

column 2, reference 3, beginning with "Hall, R.C. and Harris, D.E." and ending with "245-259." should have inserted after "vol. 169," the date -- 1979 --.

Signed and Sealed this

Seventh Day of December, 1993

*Attest:*

BRUCE LEHMAN

*Attesting Officer*     *Commissioner of Patents and Trademarks*